United States Patent [19]

Markart et al.

[11] Patent Number: 4,509,859
[45] Date of Patent: Apr. 9, 1985

[54] APPARATUS FOR OPTOELECTRONIC EVALUATION OF TEST STRIPS

[76] Inventors: Ernst Markart, Liebensteinstrasse 14, 8000 München 60; Reinhard Blümel, Strassberger Strasse 23, 8000 München 40; Holger Eggert, Holzstrasse 20, 8000 München 5, all of Fed. Rep. of Germany

[21] Appl. No.: 360,352

[22] Filed: Mar. 22, 1982

[30] Foreign Application Priority Data

Mar. 26, 1981 [DE] Fed. Rep. of Germany ....... 3112028
Mar. 26, 1981 [DE] Fed. Rep. of Germany ....... 3112031

[51] Int. Cl.³ ............................................ G01N 21/47
[52] U.S. Cl. .................................... 356/446; 356/243; 422/68
[58] Field of Search ................................ 356/445–448, 356/243; 422/56, 68

[56] References Cited

U.S. PATENT DOCUMENTS 4,015,904 4/1977 De Remigis ...................... 356/243
4,268,173 5/1981 Barnard et al. ..................... 356/445

Primary Examiner—Vincent P. McGraw
Attorney, Agent, or Firm—Peter K. Kontler

[57] ABSTRACT

Test apparatus for the optoelectronic evaluation of test paper strips such as are used, for example, for determining the blood sugar level, which apparatus may be calibrated in a simple and accurate manner. For dark calibration, there is provided in a position opposite the light source and the photosensor a reflector having a black reflector surface, with the space for receiving the test paper strip - as determined by the holding means - being located between the light source and the photosensor on the one hand and the reflector on the other hand. There are provided accuracy-improving means for the test paper-dependent calibration of the evaluation and display means and a bar code reader comprising a channel for passing therethrough a bar code strip, a light source for illuminating the bar code strip and a photosensor to scan the bar code pattern and having its output connected to the evaluation and display means (FIG. 1).

14 Claims, 4 Drawing Figures

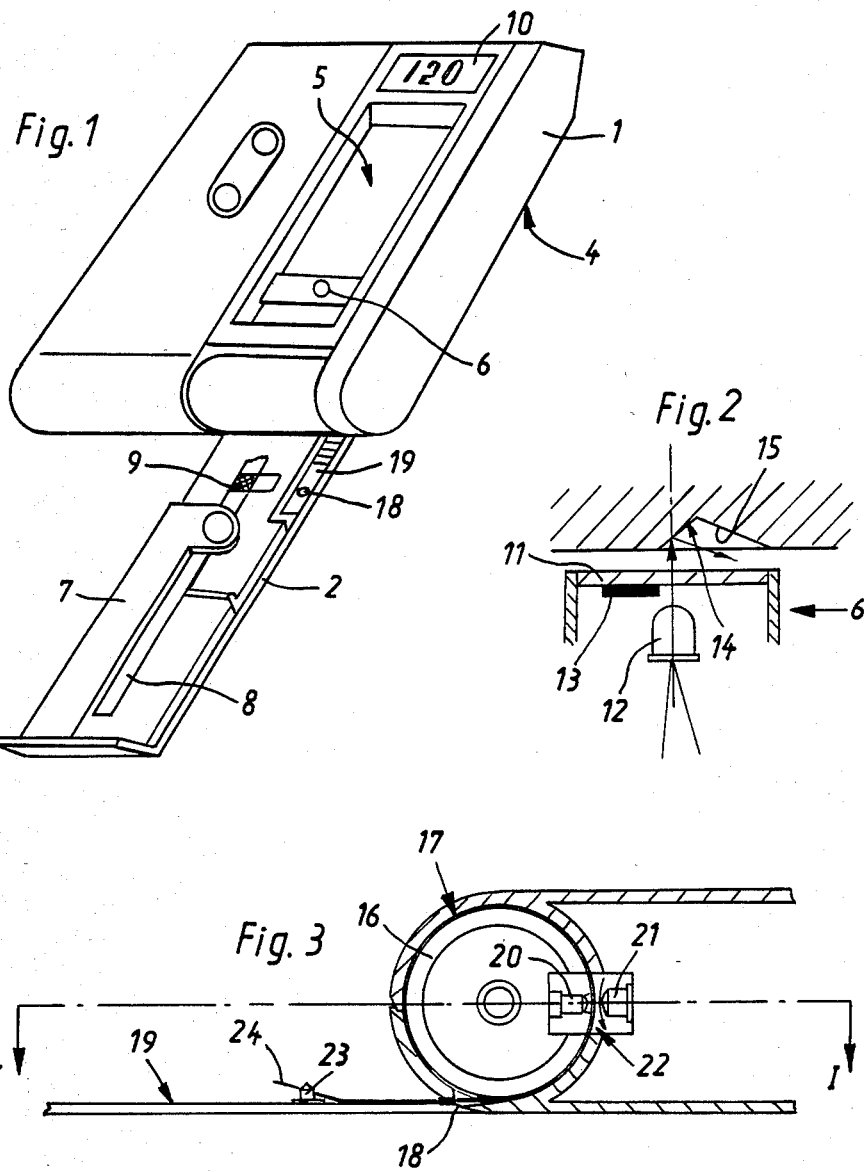

APPARATUS FOR OPTOELECTRONIC EVALUATION OF TEST STRIPS

BACKGROUND OF THE INVENTION

The invention relates to test apparatus for optoelectronically evaluating test paper strips such as are used for determining blood sugar levels, comprising a case having a battery compartment and means for holding the test paper strip, a light source illuminating the test paper strip, a photosensor receiving the light reflected from the test paper strip, and calibratable electronic evaluation and display means receiving and controlled by the photosensor output.

The invention relates to an improvement of the optoelectronic test device-including the light source and the photosensor-in regard to the dark-calibration of the test apparatus.

The known devices of the type specified above must be calibrated before each use, requiring a so-called light-calibration, which is performed on the untreated, i.e. not yet discolored test paper strip, and a so-called dark-calibration, which is performed on a separate black calibrating strip. Apart from the fact that the necessity of performing a dark-calibration each time the device is put into use is far from user-friendly, dark-calibration by means of the black calibrating strip is not too accurate because the absorptive properties of the black calibrating strip may change after repeated use due to dirt, skin grease and finger stains or prints.

Also, this type of test apparatus is used in connection with test paper strips which have a chemically active section. The producers of these strips do in fact try to make them as uniform as possible in quality. Still, it cannot be avoided that the reaction properties turn out to differ substantially between production batches.

In the case of test paper strips for determining blood sugar levels, one and the same blood sugar content may in fact cause test paper strips of one batch to become darker than test paper strips from another batch. In the past, this uncertainty had to be accepted although it constituted a substantial disadvantage.

SUMMARY OF THE INVENTION

An object of the invention is to so design a test device of the type outlined above that the aforesaid disadvantages are eliminated and that the device may be calibrated more simply and more accurately, at the same time providing accuracy-improving means for the test paper-dependent calibration of the evaluation and display means.

In accordance with the invention, this object is attained by providing for the dark-calibration a reflector having a black reflector surface opposite the light source and the photosensor, with the space for receiving the test paper strip as determined by the holding means being located between the light source and the photosensor on the one hand and the reflector on the other hand.

As a consequence, no separate calibrating strip need be inserted for dark-calibrating the device, although the latter will be necessary as before. Also, dark-calibration will be more accurate than in the past because it will not be necessary any more to touch the reflector inside the device-in contrast to the prior art black calibrating strip-whereby that strip cannot become dirty as in the past.

According to another feature of the invention the reflector has a planar black and glossy reflector surface, with the light source being laterally offset from a line normal to the reflector surface and the photosensor being arranged on that same side of said line normal, but at a greater distance therefrom.

As a result, the black reflector, which is in the form of a so-called black mirror, will reflect away from the photosensor the light impinging on it from the light source so that the arrangement-seen from the photosensor-acts as a so-called black hole, which has excellent absorption properties. Conveniently, a test device of the type outlined above will include for the test paper-dependent calibration of the evaluation and display means a bar code reader which has a channel for passing therethrough the bar code strip, a light source for illuminating the bar code strip and a photosensor which scans the bar code and of which the output is applied to the evaluating and display means.

In this connection, the invention contemplates the use of a calibrating strip (supplied by the manufacturer) which bears the batch specifications essential to the calibration in the form of a so-called bar code, i.e. an optoelectrically readable pattern of dark and light or transparent bars. This kind of bar code is used frequently on food packages to be registered by automatic cash register installations.

As a result, each measurement will be based on a calibration of the evaluation and display means which takes into account the specifications of each batch of test strips so that measurements will be free of variations among batches and a higher test accuracy will be obtained.

Advantageously, the light source is provided on one side and the photosensor on the other side of the channel to make possible the use for calibration of a transparent bar code strip bearing opaque bars.

This way the test device may be provided in a very compact shape. Also, the bar code provides sharply defined light-to-dark transitions so that the pattern will be read more safely, reducing the probability of reading errors.

According to another feature of the invention, the case has a flap-type cover member mounted on a shaft for pivoting movement between a closed position in which the cover member engages the top surface of the case and an open position in which both the cover member and the bottom surface of the case engage a support such as a tabletop, said shaft supporting a drum member which for receiving the bar code strip has at one end thereof an annular groove-like slot concentric with said shaft and including a tangential opening to the inside surface of the cover member, the latter having support means for the bar code strip. At the same time, the light source and the photosensor are arranged laterally of the slot in the case, with the space between the light source and the photosensor defining the afore-mentioned channel.

This way, operation of the test apparatus will be straightforward and user-friendly. The user who opens a fresh package of test paper strips proceeds to push the bar code strip included in that package into the annular groove-like slot in the open position of the cover, whereby the slot will convolute or coil the leading portion of the bar code strip on a circular arc; the trailing end of the bar code strip will be secured to the strip holding means. For measurement, the user moves the cover member from the open position to the closed position, causing the bar code on the circularly coiled section of the bar code strip to be passed automatically by the light source and the photosensor, during which passage the bar code will be read.

The invention will now be described with reference to the appended drawings.

BRIEF DESCRIPTION OF THE DRAWINGS

FIG. 1 is a perspective view of test apparatus according to the invention with the cover member in its open position;

FIG. 2 is a simplified sectional view depicting the optoelectronic means and the reflector;

FIG. 3 is a longitudinal sectional view of the apparatus of FIG. 1; and

DESCRIPTION OF THE PREFERRED EMBODIMENTS

Figure 4:
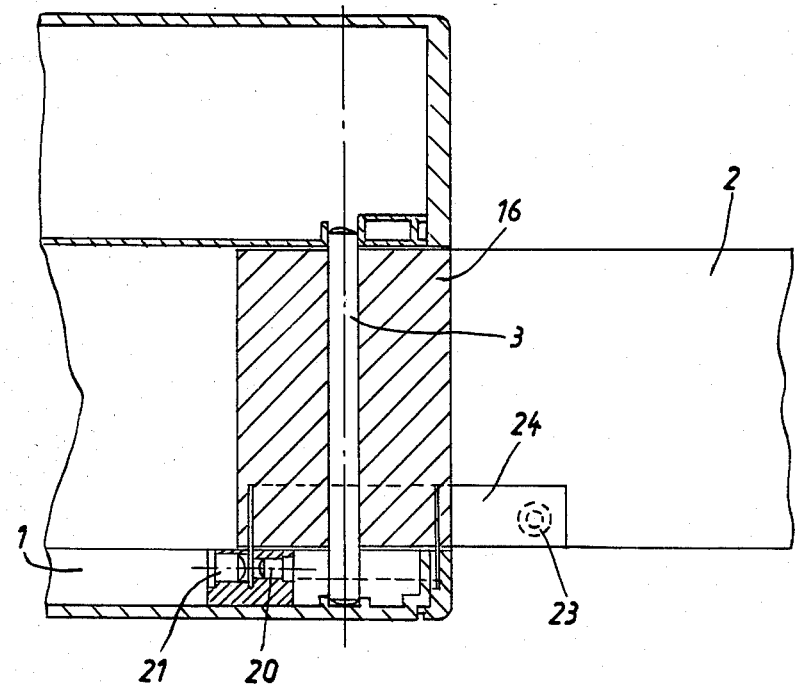
FIG. 4 is a sectional view as seen from line I—I of FIG. 3.

As shown in FIG. 1, the test apparatus of the subject invention has a case 1 and a flap-type cover member 2. Cover member 2 is mounted for pivoting movement on a shaft 3 (see FIG. 4). In the open position shown in FIG. 1, both cover member 2 and bottom surface 4 of the case engage a support such as a tabletop. In the closed position cover member 2 engages top surface 5 of the case, covering and concealing the optoelectronic test means 6.

On cover member 2 is provided holding means 7 for a test paper strip 8. In the closed position, cover member 2 places the chemically active leading end 9 of test paper strip 8 on optoelectric test means 6 so that this chemically active end 9, which may be disclosed, may be evaluated optoelectrically. An evaluating means (not shown) outputs the test results to an LCD display 10.

FIG. 2 shows details of optoelectric test means 6. The light source comprises a light-emitting diode (LED) 12 seated behind a window 11 in top surface 5 of the case; the photosensor comprises a photovoltaic element or photoresistor 13. In a position opposite test means 6 there is provided in cover member 2 a reflector 15 of which the black and glossy reflector surface 14 extends at an angle. The inclination is such that LED 12 will be laterally offset from a line normal to reflector surface 14 while photoresistor 13 is located on the same side as this normal line, but is offset at a greater distance therefrom than is the LED 12. By virtue of this arrangement, the light from LED 12 will be reflected away from the photoresistor. This arrangement defines opposite the photoresistor 13 a so-called black hole; the light coming from this black hole and received by photoresistor 13 is the residual light to be measured for dark-calibration.

Shaft 3 of cover member 2 supports a drum 16 which has at one end thereof an annular groove-like slot 17 concentric with shaft 3. Slot 17 includes a tangential opening 18 to the inner surface 19 of cover member 2. Laterally of slot 17, case 1 mounts a light source 20 and a photosensor 21. The bar code strip support on cover member 2 is in the form of a clamp button 23. Bar code strip 24 will be pushed into slot 18 from the left (in FIG. 3); in the process, it will be convoluted or coiled on a circular arc. The trailing end of bar code strip 24 has a hole therein and may be clamped down therewith on buttom 23.

Bar code strip 24 carries the bar code on the outer surface thereof. This section of strip 24 moves through a channel 22 between light source 20 and photosensor 21.

As the user moves cover member 2 from the open position shown in FIG. 1 to its closed position by pivoting it in a clockwise direction, the bar code will run through between light source 20 and photosensor 21 during such pivoting movement and will be read into the device.

It is to be understood that the embodiments shown herein are susceptible to convenient modification without departing from the essential thought underlying this invention.

As a result of the disclosed invention, each measurement will be based on a calibration on the basis of the specifications of each batch; measurements will not be affected by variations among the various batches and the obtainable accuracy will be much higher than was attainable in the past.

We claim:

1. Test apparatus for optoelectronically evaluating test strips, for example those used in determining blood sugar levels, comprising means for holding a test strip to be evaluated; a light source for illuminating the test strip; a sensor for receiving light which is reflected from the test strip; and calibrating means including a reflector disposed opposite said light source and sensor and defining therewith an elongated gap for the test strip, said reflector having a reflector surface facing across said gap and being oriented to reflect light which issues from said source away from said sensor while said gap is empty.

2. Test apparatus as defined in claim 1, further comprising a case for said calibrating means, said light source and said sensor.

3. Test apparatus as defined in claim 1, wherein said reflector surface is black, planar and glossy.

4. Test apparatus as defined in claim 1, wherein said light source and said sensor are laterally offset from and are both disposed at one side of a line which is normal to said reflector surface, as considered in the longitudinal direction of said gap, said sensor being more distant from said line than said light source.

5. Test apparatus as defined in claim 1, wherein said reflector constitutes for said sensor a black hole with a highly pronounced light absorptivity.

6. Test apparatus as defined in claim 1, wherein said sensor is arranged to receive only diffused light when said light source emits light while said gap is empty.

7. Test apparatus for optoelectronically evaluating test strips, for example those used in determining blood sugar levels, comprising means for holding a test strip to be evaluated; a light source for illuminating the test strip; a sensor for receiving light which is reflected from the test strip; dark-calibrating means including a reflector disposed opposite said light source and said sensor and defining therewith an elongated gap for the test strip, said reflector having a black reflector surface facing across said gap; bar-code reading means for the test strip-dependent calibration of calibratable electronic evaluation and display arrangements which receive signals from said sensor.

8. Test apparatus as defined in claim 7, wherein said bar code reading means includes means defining a channel for passage therethrough of a bar code strip, an additional light source for illuminating the bar code strip, and an additional light sensor for scanning a bar code on the strip and for generating an output signal to be applied to the evaluation and display arrangements.

9. Test apparatus as defined in claim 8, wherein the bar code strip transmits light and the bar code is opaque, said additional light source and said additional light sensor being located at opposite sides of said channel so that light passing between them travels through a bar code strip located between them in said channel.

10. Test apparatus as defined in claim 9, further comprising a case for said calibrating means, said light sources and said sensors, said case having a top surface, a bottom surface, and a flap-type cover member pivotable between a closed position in which it overlies at least a part of said top surface and an open position in which said cover member and said bottom surface and positioned to engage a support.

11. Test apparatus as defined in claim 10: further comprising a shaft in said case and mounting said cover member for pivotal movement between said open and closed positions thereof.

12. Test apparatus as defined in claim 11, further comprising a drum supported on said shaft and having an end portion provided with an annular groove concentric with said shaft for receiving the bar code strip therein, said groove having a tangential opening extending to an inner surface of said cover member which faces said top surface when said cover member is in said closed position thereof.

13. Test apparatus as defined in claim 12, further comprising additional holding means for the bar code strip, said additional holding means being mounted on said inner surface and said additional light source and said additional sensor being laterally offset from said groove, said channel being at least in part defined by said additional light source and said additional sensor.

14. Test apparatus for optoelectronically evaluating test strips, for example those used in determining blood sugar levels, comprising means for holding a test strip to be evaluated; a light source for illuminating the test strip; a sensor for receiving light which is reflected from the test strip; and calibrating means including a reflector having a surface disposed opposite said light source and said sesnor, said reflector defining with said light source and said sensor an elongated gap for the test strip, said light source and said sensor being laterally offset from and being both disposed at one side of a line which is normal to said surface, as considered in the longitudinal direction of said gap, and said sensor being more distant from said line than said light source.

* * * * *